United States Patent [19]

Fujimoto

[11] Patent Number: 4,776,668
[45] Date of Patent: Oct. 11, 1988

[54] IMAGE FOCUSING OCULAR PIECE FOR A VIEWING SCOPE INCLUDING MECHANISM FOR ACCOMMODATING DIFFERENTIAL EXPANSION

[75] Inventor: Isao Fujimoto, Tenafly, N.J.

[73] Assignee: Machida, Inc., Orangeburg, N.Y.

[21] Appl. No.: 817,354

[22] Filed: Jan. 9, 1986

[51] Int. Cl.[4] ............ G02B 23/26; G01N 21/16; A61B 1/00

[52] U.S. Cl. ............ 350/96.26; 350/96.25; 350/253; 356/241; 128/4; 128/6

[58] Field of Search ........... 350/96.24, 96.25, 96.26, 350/253, 533, 96.18, 96.20, 96.22; 356/241; 128/4, 6

[56] References Cited

U.S. PATENT DOCUMENTS

| 1,325,936 | 12/1919 | Fouasse | 350/253 |
|---|---|---|---|
| 2,975,785 | 3/1961 | Sheldon | 350/96.26 |
| 4,045,129 | 8/1977 | Hamar | 350/253 X |
| 4,063,796 | 12/1977 | Hiltebrandt | 128/4 X |
| 4,182,547 | 1/1980 | Siegmund | 350/96.26 |
| 4,236,790 | 12/1980 | Smith | 350/253 |
| 4,294,233 | 10/1981 | Takahashi | 128/4 |
| 4,323,304 | 4/1982 | Ishii | 128/6 X |
| 4,329,980 | 5/1982 | Terada | 128/4 |
| 4,336,794 | 6/1982 | Chikama | 128/4 |
| 4,390,012 | 6/1983 | Mizumoto | 128/4 |
| 4,687,288 | 8/1977 | Margolin et al. | 350/96.20 |
| 4,711,518 | 12/1987 | Shank et al. | 350/96.20 |

FOREIGN PATENT DOCUMENTS

| 179905 | 10/1954 | Austria | 128/4 |
|---|---|---|---|
| 548462 | 10/1942 | United Kingdom | 128/4 |

Primary Examiner—William L. Sikes
Assistant Examiner—Brian M. Healy
Attorney, Agent, or Firm—Cushman, Darby & Cushman

[57] ABSTRACT

A viewing scope is described having a two-part ocular piece which assures that strain due to probe flexing does not build-up and cause breakage in a quartz silica or other similarly rigid fiberoptic image bundle. The ocular piece includes a holder which maintains the image end of the image bundle in a predetermined position with respect to the ocular parts necessary to focus the image, and a body portion to which the outer tubular cover of the probe is secured. The connection between the holder and body allows limited translational movement between the same so that differential longitudinal expansion between the image bundle and the remainder of the probe can be accommodated.

7 Claims, 2 Drawing Sheets

IMAGE FOCUSING OCULAR PIECE FOR A VIEWING SCOPE INCLUDING MECHANISM FOR ACCOMODATING DIFFERENTIAL EXPANSION

BACKGROUND OF THE INVENTION

The present invention relates to viewing scopes and, more particularly, to an image focusing ocular piece for such a viewing scope enabling image transmission media which might be damaged due to flexing, such as quartz silica fiberoptic bundles, to be used with many traditionally designed viewing scope probes.

Fiberoptic viewing scopes are now widely used to facilitate the visual checking of an operation or state which otherwise is hidden from view. For example, such scopes are used in the medical field to provide non-invasive views internally of a human body for exploration or during treatment. Fiberoptic viewing scopes utilized in the medical industry typically are known as endoscopes. Viewing scopes also find industrial applications in non-destructive testing, to view the interior of engines or the like, etc. Industrial viewing scopes are generally referred to as borescopes.

A fiberoptic viewing scope most often includes an elongated probe or insertion tube which terminates in a probe head at a distal tip. An image transmission medium, such as a fiberoptic bundle, extends through the probe to the head for transmission of the image to be viewed to an image focusing ocular piece positioned at the exterior of the body or object under investigation. The ocular piece typically includes an eyepiece containing lenses to intercept the image from the transmission medium and focus it for viewing. In some instances, the ocular piece is adapted to be secured to a camera or the like to enable a photograph of the image to be taken.

An illuminating light guide also is often provided as part of a viewing scope, extending from the ocular piece through the probe to the probe head. The purpose of the light guide, generally also a fiberoptic bundle, is to convey illuminating light from the exterior of the body or object being viewed, to the probe head or tip, i.e., the viewing point. Control wires or other elongated elements also commonly extend through a probe outer cover to a probe head. Some viewing scopes even include working channels extending through the probe to permit passage of operating instruments to the distal tip.

Fiberoptic bundles used for image transmission generally are made from glass or plastic strands clad with a material of lower refractive index. While bundles of fiberoptic strands made from such materials are satisfactory for many purposes, they do have some limitations. For example, because of light loss in such standard fiberoptic materials, the length of instruments requiring image transmission with high resolution and discrimination is limited to about three meters.

The art is turning to fiberoptic bundles made from quartz silica fiber strands as image transmission media. The light loss from a quartz silica bundle is significantly smaller than the light loss from the same length of a fiberoptic bundle of glass and/or plastic strands. This results in viewing scopes utilizing quartz silica fiber bundles for image transmission having probes as long as 100 meters to provide effectively the same light transmittance one can obtain from a fiberoptic bundle made from glass and/or plastic having a length of 6 meters. Moreover, quartz silica fibers also are generally resistant to the effects of atomic radiation; are capable of transmitting ultra-violet light (useful in non-destructive testing); can transmit high power/energy laser light; are resistant to heat; and provide excellent color transmission. Unfortunately, one characteristic of quartz silica fiberoptic bundles has limited their wide usage. That is, quartz silica fibers are significantly less flexible than standard glass and plastic fibers. Thus, they are incapable of withstanding relatively small radius bending or flexing without incurring damage. Bending or flexing beyond the quartz silica elastic limit can result in fiber breakage or fracturing and corresponding destruction of the image bundle or, at the minimum, of image clarity. Thus, although manufacturers have incorporated quartz silica fibers in their traditional flexible viewscope designs, they have found that acceptable flexibility has been greatly diminished.

SUMMARY OF THE INVENTION

The present invention provides a construction for a viewing scope which reduces stress build-up due to flexing, in an image transmission medium contained within the probe. It therefore enables the use of an image bundle formed from quartz silica fibers in many situations in which their use has not in the past been practical. In this connection, it has been found that such stress build-up is a major cause of breakage.

The invention accomplishes this function by providing a two-part ocular piece for the viewing scope. One part is a holder for the eyepiece lenses or the like ocular members which are necessary in such a scope for receiving the image conveyed by the image transmission medium. Such holder includes means for rigidly securing the image conveying end of the transmission medium in a predetermined position with respect to the ocular members. The second part of the piece is a body to which the outer tubular cover of the probe is secured. The connection provided between the two parts of the ocular piece is selected to allow limited translational movement between the holder and body to accommodate any differential expansion between the image bundle and the probe outer cover. Thus, limited differential expansion between the image transmission medium and the probe outer cover is permitted to prevent the build-up of internal stresses in the image bundle that generally occurs in conventional viewing scopes during flexing or coiling.

Most desirably, the illuminating light guide which extends through the probe enters the same through the body portion of the ocular piece, as opposed to the holder portion. This will assure that the light guide medium will not restrict translational movement of the holder portion and, hence, the image conveying end of the transmission medium. Further, all portions of the viewing scope which extend through the elongated probe are preferably unattached to the transmission medium so that the latter will be free to expand in length or translate throughout its full length. The probe end of the image transmission medium at the distal tip of the probe is secured along with the light guide to the probe head.

The connection between the two parts of the ocular piece is designed to prevent rotation of the holder while allowing the desired translational movement. This is achieved by means of a pin in one of the parts riding within a registering slot in the other of such parts.

BRIEF DESCRIPTION OF THE DRAWINGS

With reference to the accompanying two sheets of drawings.

DETAILED DESCRIPTION OF THE PREFERRED EMBODIMENT

Figure 1:
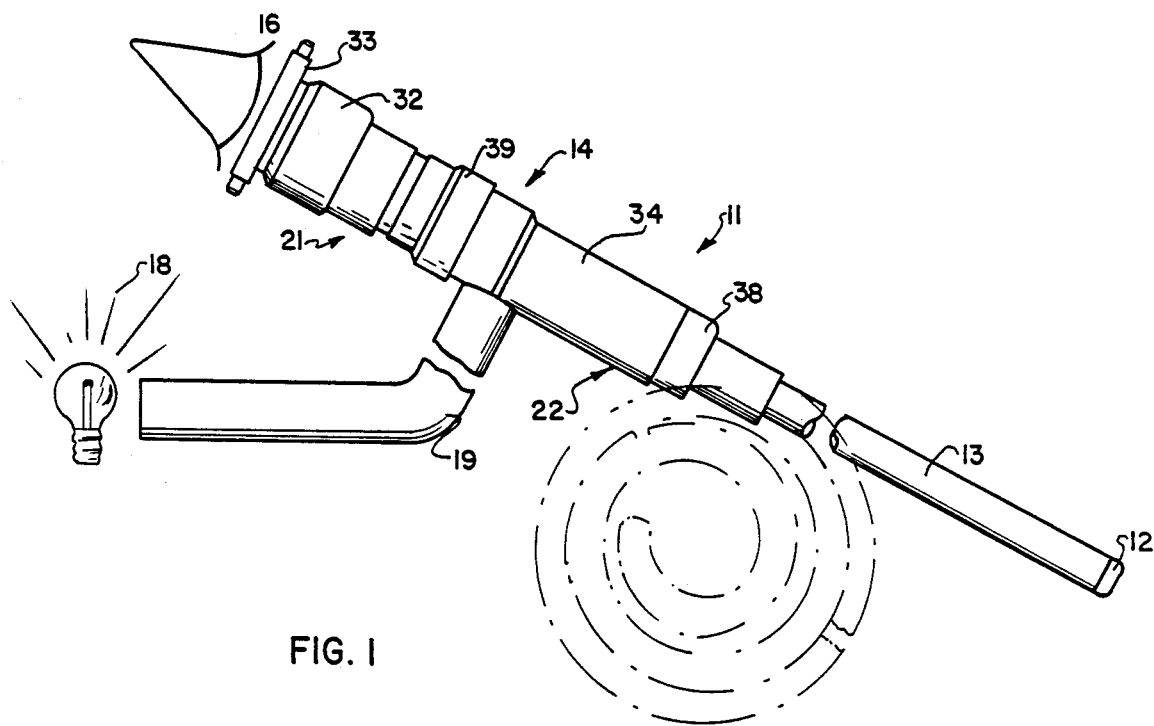
FIG. 1 is an overall broken view of a schematic representation of a viewing scope incorporating the invention.

A schematic representation of a viewing scope incorporating the present invention is generally referred to in FIG. 1 by the reference numeral 11. A viewing scope of this type is utilized to convey the image of a view at its probe distal tip or probe head 12 through a probe 13 and an ocular piece 14 to a viewing entity, such as is represented by the eye 16. The length of the probe and, hence, the distance there can be between the viewer and the probe head is dependent on, among other things, the image resolution and discrimination which is required. While these factors will vary considerably depending upon the use to which the viewing scope is placed, in most typical applications the length of the probe typically is limited to three meters if the light transmission medium utilized with the same is a fiberoptic bundle having conventional glass or plastic strands.

Scope 11 includes as is common, means for illuminating a scene to be viewed. A light guide in the form of an incoherent fiberoptic bundle 17 extends between a source of illumination schematically represented at 18 and the probe head. A light guide cable 19 is provided housing the light guide between the light source and the viewing scope. The light guide extends through the ocular piece as illustrated in FIG. 2 and coaxially with the image transmission medium through the probe to the probe head 12, where the image medium and light guide are secured.

Figure 2:
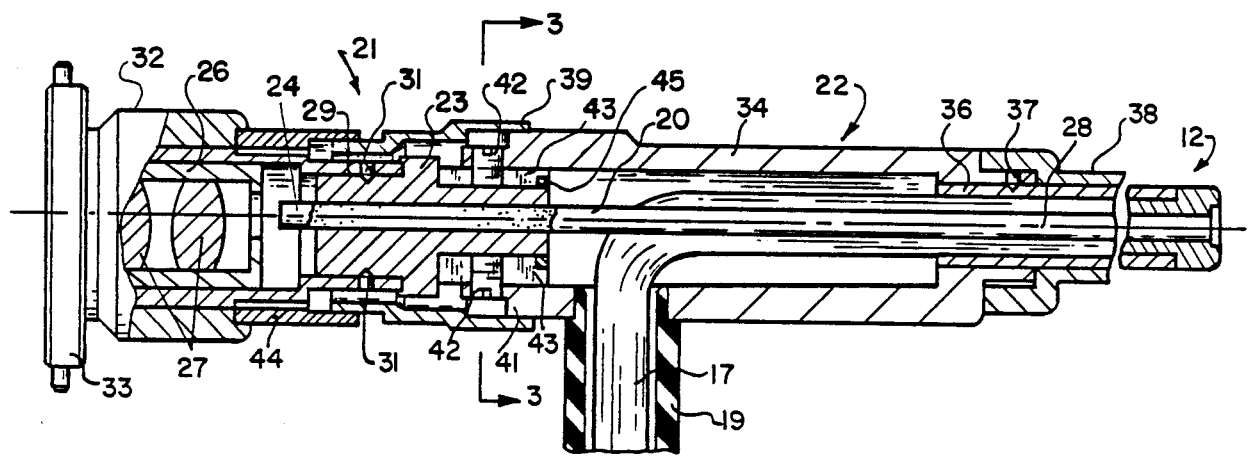
FIG. 2 is an enlarged, broken away and sectional view of the viewing scope of FIG. 1, primarily illustrating the image focusing ocular piece thereof and its relationship to the probe.
Figure 3:
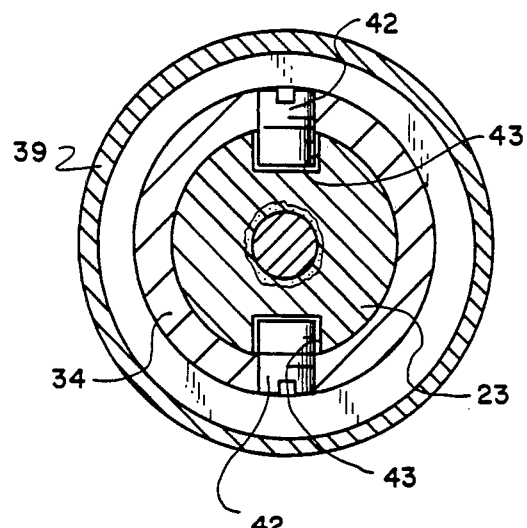
FIG. 3 is a sectional view taken on a plane indicated by the lines 3—3 in FIG. 2.

The image transmission medium is a coherent fiberoptic bundle of pure quartz silica strands, as represented in FIG. 2 at 20. (The strands are coated, of course, with a material of lower refractive index to assure capture of light.) As mentioned previously, while the advantages of quartz silica fiberoptic bundles has been realized for some time, their usage in traditional viewing scopes has been limited. This limitation has been due primarily to the fact that quartz silica fiberoptic bundles are incapable of withstanding the amount of flexing which is desirable in a viewing scope. The instant invention provides an image focusing ocular piece for a viewing scope which enables the use of a quartz silica fiberoptic bundle for an image transmission medium in many situations in which flexibility has prevented or limited effective use in the past. It has been recognized that a significant portion of the breakage in a quartz silica fiberoptic bundle when used in a viewing scope has been due to stresses created in the bundle when differential expansion occurs between the bundle and other portions of the viewing scope probe upon probe flexing. The image focusing ocular piece of the invention compensates for this differential expansion by providing a two-part arrangement which enables the fiberoptic bundle to be made free of all aspects of the probe along the length of such bundle, except for the probe head and the ocular parts necessary to receive an image conveyed by the bundle and convert it by focusing or the like, to the desired state. To this end, the ocular piece 14 includes both a holder portion 21 and a body portion 22.

As best illustrated in FIG. 2, the holder portion includes a main holder body 23 which rigidly secures the end 24 of the fiberoptic bundle in a set position with respect to an eyepiece cup 26 which, in turn, rigidly maintains the ocular parts represented by the lenses 27 in a set relationship along the optical axis of the ocular piece as represented at 28. A tubular sleeve 29 maintains such relationship by receiving and being rigidly secured to the cup 26. As illustrated, such sleeve also receives the body 23 and is maintained in position with respect to such body by set screws 31. The holder includes, as is conventional, a diopter adjustment ring 32 and its accompanying adjustment mechanism, as well as a camera lock ring-pin arrangement 33.

The body portion 22 of the ocular piece is principally comprised of a main tubular body 34. The probe 13 includes an outer tubular cover 36 which is received into and retained in one end of the main body via a plurality of set screws, one of which is represented in FIG. 2 at 37. An outer body cover 38 of a flexible material or the like encases the junction between the body and outer probe cover.

In keeping with the invention, the connection between the holder and body allows limited translational movement between the two portions. That is, the holder portion 21 includes an exterior tubular cover 39 which receives a complementary tubular end 41 of the main body for limited telescopic motion between such cover and the fiberoptic bundle holder 23. Two guide pins 42 project from the main body 22 at diametrically opposed positions into registering slots 43 in the holder 23. It will be recognized that this pin-slot combination permits the desired limited translational motion while preventing rotation between the two parts and consequent image orientation variation. A stopper 45 is mounted in each of slots 45 to retain pins 42 in the slots. A covering sleeve 44 is provided between the adjustment ring 32 and guide pin cover 39. Cover 39 and sleeve 44 are longitudinally spaced as a result of adjusting bundle end 24 relative to lenses 27 during assembly.

It will be recognized from the above that the two-part construction of the ocular piece separates the rigid securance between the image bundle and the ocular parts that is necessary from the connection with the probe outer cover 36. Thus, differential longitudinal expansion of the outer cover and the image bundle is accommodated. Most desirably, the image bundle is unattached to the probe cover for the full length of the probe between the probe head and the ocular parts so that flexing anywhere along the length of the probe will be accommodated.

The light guide cable 1 with its accompanying light guide 17 is secured to the body part 22, as opposed to the holder part 21 of the ocular piece. Moreover, it is not secured to the image bundle. The result is that the light guide will not interfere with translational movement of the image bundle relative to the probe outer cover. The fiberoptic bundle of the light guide 17 can be made up of conventional glass or plastic strands which do not suffer from the same strain problems upon flexing as quartz silica strands. Special provisions therefore need not be made for the same. Although as illustrated means are provided securing both the probe end of the light guide and image bundles to the probe head, they are not otherwise attached to one another throughout the full length of the probe. Thus, the light guide bundle will not interfere with free longitudinal expansion of the image bundle and ocular part holder relative to the remainder of the viewing scope. It will be recognized that it is most desirable that no other mechanism which might be provided through the probe be attached to the image bundle if such mechanism may experience longitudinal expansion during flexing which is different than that which may be experienced by the image bundle, (except, of course, at the probe head.

Figure 4:
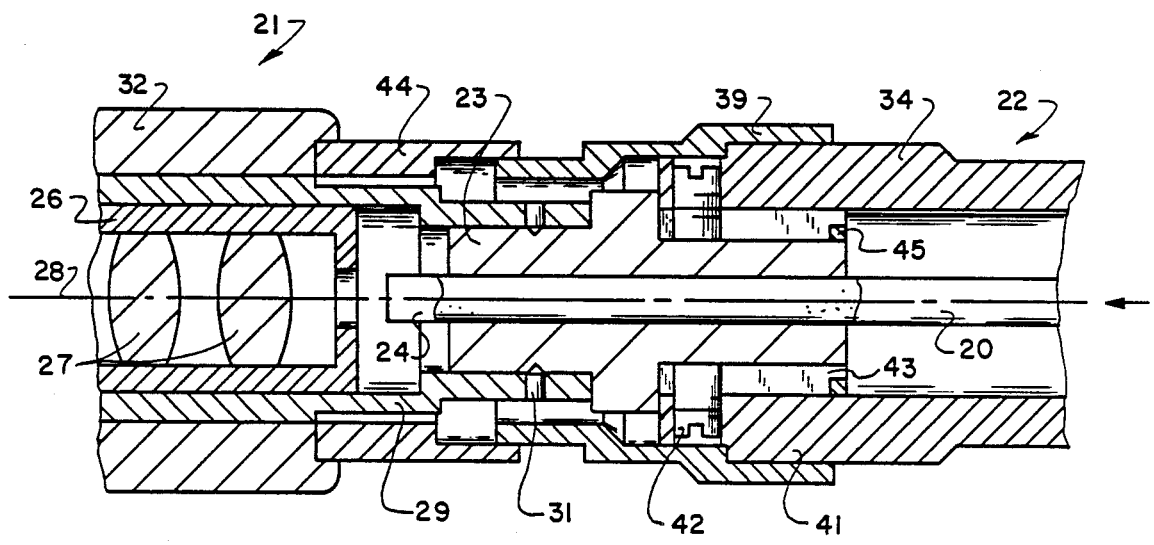
FIG. 4 is an enlarged sectional view of the image focusing ocular piece illustrating the parts thereof in an alternate position.

FIG. 1 includes a phantom showing of the coiling of a probe typical during packaging of a viewing scope for shipment. FIG. 4 illustrates resulting differential longitudinal expansion. That is, as illustrated, the body part 22 of the ocular piece has moved to the left as illustrated in FIG. 1 relative to the holder part 21. The rigid relationship of the image transmission bundle to the ocular parts is maintained, although differential longitudinal expansion between the probe image bundle and the remainder of the probe parts is accommodated.

The invention has been described in connection with a preferred embodiment thereof. It will be recognized, however, by those skilled in the art that various changes can be made without departing from the spirit of the invention. For example, although the body portion of the ocular piece telescopes within the holder in this preferred arrangement, the reverse may be found in some situations to be desirable. Moreover, although it is preferred that the guide pin and slide arrangement be as described in order to facilitate access to the guide pins, such pins could extend from the holder part whereas the complementary slots are provided in the body part. It is therefore intended that the scope of coverage provided applicant be determined only by the language of the claims and its equivalent language.

What I claim is:

1. An image focusing ocular piece for a viewing scope having an elongated probe which includes an image transmission medium to convey an image from a probe head to the image focusing ocular piece, said ocular piece comprising:

a holder for the ocular parts necessary to receive an image conveyed by said medium and convert said image to a desired focus, said holder including means for securing an image conveying end of said transmission medium in a predetermined position with respect to said ocular parts;

a body to which an outer tubual cover of said elongated probe is secured; and wherein the connection between said holder and said body allows limited translational movement between the same; and said image transmission medium is secured to said probe head and to said holder for translational movement therewith but otherwise is free is securance within said viewing scope for translational movement whereby differential longitudinal expansion of said body and said holder is accommodated.

2. An image focusing ocular piece according to claim 1 wherein said image transmission medium is an elongated bundle of quartz silica fiberoptic fibers.

3. An image focusing ocular piece according to claim 1 wherein a light guide extends into said body part of said ocular piece and along the length of said probe within said outer cover to terminate at said probe head; and a source of illuminating light is provided for transmission by said light guide to said probe head.

4. An image focusing ocular piece according to claim 3 wherein the ends of both said image transmission medium and said light guide at said probe head are rigidly secured thereto but are unattached relative to one another between said head and said body.

5. An image focusing ocular piece according to claim 1 wherein said connection includes first end portions of said body holder, and an exterior tubular cover within which complementary end portions of said body and holder are received for limited telescopic motion.

6. An image focusing ocular piece according to claim 5 wherein a first one of said holder and body includes a pin which rides in a slot provided in the other of said body and holder to prevent relative rotation between said body and holder.

7. In a viewing scope having an elongated probe extending between a probe head and an image focusing ocular piece wherein the elongated probe has a flexible outer tubular covering enclosing an elongated image transmission medium for conveying an image from the probe head to the image focusing ocular piece, the combination comprising:

means rigidly securing one end of the elongated image transmission medium to said probe head;

means securing the opposite end of the elongated image transmission medium to the image focusing ocular piece in a predetermined position; and said elongated image transmission medium being unattached to said probe outer cover between said probe head and said image focusing ocular piece whereby differential longitudinal expansion of said outer cover and said image transmission medium is accommodated.

* * * * *